(12) United States Patent
Maesani et al.

(10) Patent No.: US 11,147,492 B2
(45) Date of Patent: Oct. 19, 2021

(54) NON-INVASIVE DRAWABLE ELECTRODE FOR NEUROMUSCULAR ELECTRIC STIMULATION AND BIOLOGICAL SIGNAL SENSING

(71) Applicant: ECOLE POLYTECHNIQUE FEDERALE DE LAUSANNE (EPFL), Lausanne (CH)

(72) Inventors: Andrea Maesani, Lausanne (CH); Andrea Biasiucci, Lausanne (CH); Stefano Silvio Giovanni Varricchio, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 282 days.

(21) Appl. No.: 15/509,204

(22) PCT Filed: Sep. 9, 2015

(86) PCT No.: PCT/IB2015/056897
§ 371 (c)(1),
(2) Date: Mar. 7, 2017

(87) PCT Pub. No.: WO2016/038545
PCT Pub. Date: Mar. 17, 2016

(65) Prior Publication Data
US 2017/0273590 A1 Sep. 28, 2017

(30) Foreign Application Priority Data
Sep. 10, 2014 (WO) .................. PCT/IB2014/064382

(51) Int. Cl.
| | |
|---|---|
| A61N 1/04 | (2006.01) |
| A61B 5/291 | (2021.01) |
| A61B 5/259 | (2021.01) |
| A61B 5/296 | (2021.01) |
| H01B 1/00 | (2006.01) |

(52) U.S. Cl.
CPC .............. *A61B 5/291* (2021.01); *A61B 5/259* (2021.01); *A61B 5/296* (2021.01); *A61N 1/0452* (2013.01);
(Continued)

(58) Field of Classification Search
CPC .. A61N 1/0452; A61N 1/0484; A61N 1/0496; A61N 1/04087; A61N 1/0478;
(Continued)

(56) References Cited

U.S. PATENT DOCUMENTS

| | | | |
|---|---|---|---|
| 3,610,229 | A | 10/1971 | Zenkich |
| 3,845,757 | A | 11/1974 | Weyer |

(Continued)

FOREIGN PATENT DOCUMENTS

| | | |
|---|---|---|
| DE | 2644236 A1 | 4/1978 |
| EP | 0128103 A1 | 12/1984 |

(Continued)

OTHER PUBLICATIONS

Zhang, Qin, Higher Education Press and Springer-Verlag Berlin Heidelberg, "Direct writing of electronics based on alloy and metal (DREAM) ink: A newly emerging area and its impacton energy, environment and health sciences", (Year: 2012).*

(Continued)

*Primary Examiner* — Eun Hwa Kim
*Assistant Examiner* — Adam Z Minchella
(74) *Attorney, Agent, or Firm* — Andre Roland SA; Nikolaus Schibli

(57) ABSTRACT

Non-invasive "drawable", or "paintable", electrode for electrical stimulation or biological signal sensing comprising a pervious and electrically conductive layer (1), at least one electrically insulating element (2) for maintaining the electrically conductive layer (1) separated from the skin (11), and a conductive material (3) that is deposed using a (Continued)

delivery system (4) on desired areas (5) of the electrically conductive layer (1). The conductive material (3) can penetrate the electrically conductive layer (1) and any other part of the electrode underlying the desired areas (5), thus reaching the skin. The conductive material (3) creates an electrical connection between the desired areas (5) of the electrically conductive layer (1) and the skin. Therefore, the shape of the desired areas (5) electrically connected with the skin, can be customized by the user deposing (or "drawing") the conductive material (3). Thus, the conductive material (3) enables the fabrication of electrodes with custom-shaped electrically conductive areas in desired positions.

21 Claims, 7 Drawing Sheets

(52) U.S. Cl.
CPC ......... *A61N 1/0456* (2013.01); *A61N 1/0492* (2013.01); *A61B 2562/14* (2013.01); *A61N 1/0484* (2013.01); *H01B 1/00* (2013.01)

(58) Field of Classification Search
CPC .. A61N 1/0492; A61N 1/0456; A61B 5/6804; A61B 5/25; A61B 5/259; A61B 5/27; A61B 5/257; A61B 5/266; A61B 5/268; A61B 5/265; A61B 5/04087; A61B 5/0478; A61B 5/0492; A61B 2562/14; H01B 1/00
See application file for complete search history.

(56) References Cited

U.S. PATENT DOCUMENTS

| | | | |
|---|---|---|---|
| 3,998,215 A | 12/1976 | Anderson et al. | |
| 4,867,166 A | 9/1989 | Axelgaard et al. | |
| 5,183,599 A * | 2/1993 | Smuckler | A61N 1/0496 264/104 |
| 2003/0163035 A1* | 8/2003 | Van Heerden | A61N 1/0492 600/397 |
| 2008/0082153 A1* | 4/2008 | Gadsby | A61N 1/046 607/152 |
| 2012/0016440 A1 | 1/2012 | Muccio | |
| 2013/0172722 A1 | 7/2013 | Ninane et al. | |
| 2013/0172724 A1* | 7/2013 | Ali Mohamed Aziz | A61B 5/04087 600/391 |
| 2014/0209351 A1* | 7/2014 | Reinhardt | A61N 1/0452 174/126.2 |
| 2014/0249613 A1* | 9/2014 | Kaib | A61N 1/3987 607/149 |

FOREIGN PATENT DOCUMENTS

| | | |
|---|---|---|
| WO | WO0102052 A2 | 1/2001 |
| WO | WO2007092290 A2 | 8/2007 |
| WO | WO2012140629 A1 | 10/2012 |
| WO | WO2012152418 A1 | 11/2012 |

OTHER PUBLICATIONS

International Search Report of PCT/IB2015/056897 dated Dec. 22, 2015.
Written Opinion of the International Search Authority dated Dec. 22, 2015.
Keller, Thierry, and Andreas Kuhn. "Electrodes for transcutaneous (surface) electrical stimulation." Journal of Automatic Control 18.2 (2008): 35-45.
Marc Lawrence, "Transcutaneous Electrode Technology for Neuroprostheses," ETH Zürich Dissertation, Diss. No. 18213, 2009.
Yu, Yang, Jie Zhang, and Jing Liu. "Biomedical implementation of liquid metal ink as drawable ECG electrode and skin circuit." PLoS One 8.3 (2013): e58771.

* cited by examiner

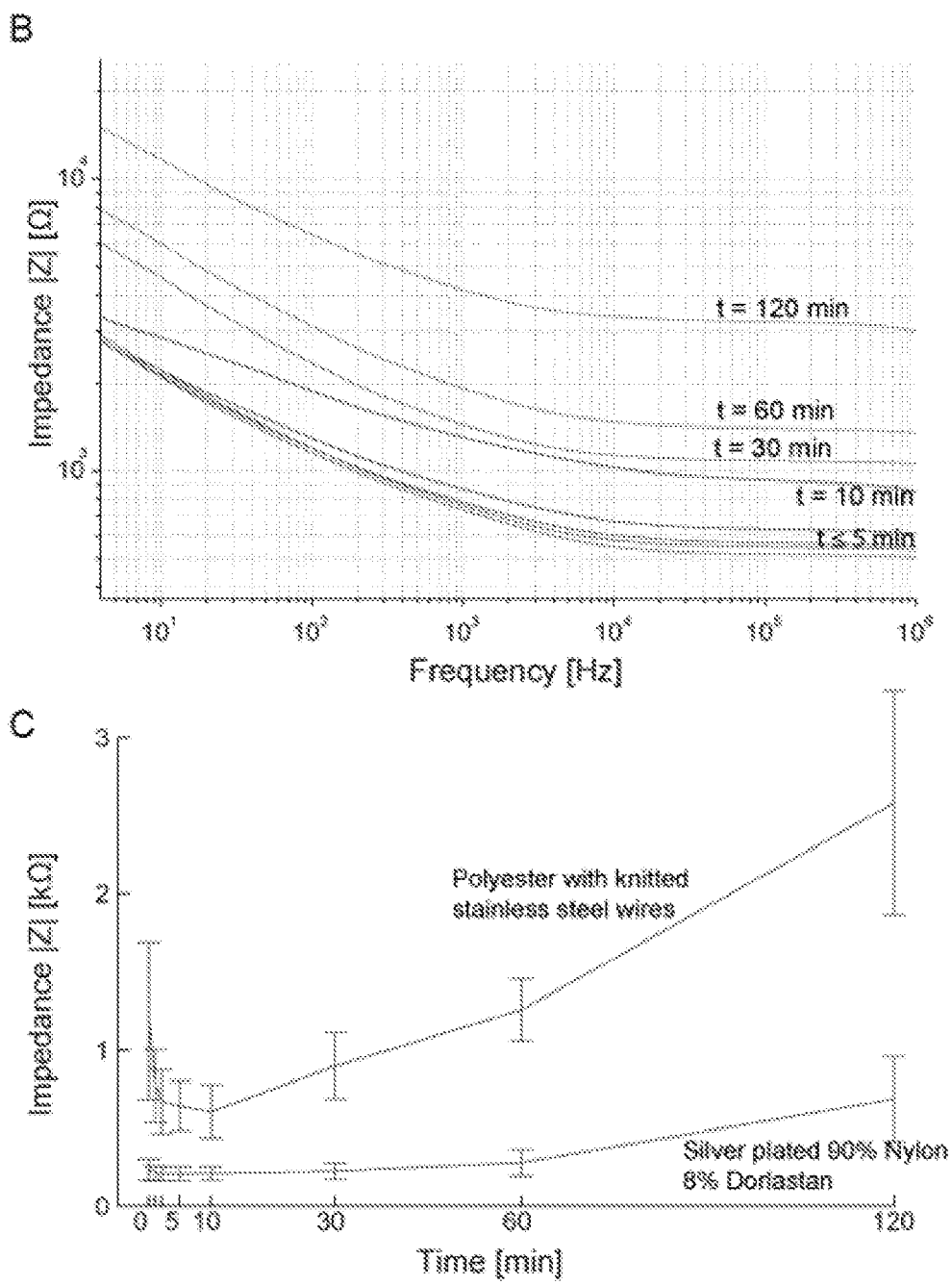

NON-INVASIVE DRAWABLE ELECTRODE FOR NEUROMUSCULAR ELECTRIC STIMULATION AND BIOLOGICAL SIGNAL SENSING

CROSS REFERENCE TO RELATED APPLICATIONS

The present application is a U.S. national stage application of PCT/IB2015/056897 filed on Sep. 9, 2015 designating the United States, and claims foreign priority to International patent application PCT/IB2014/064382 filed on Sep. 10, 2014, the contents of both documents being herewith incorporated by reference in their entirety.

TECHNICAL FIELD

The present invention is related to non-invasive electrodes for transcutaneous electrical stimulation or for biological signals sensing.

BACKGROUND ART

Several devices for biomedical, sport or wellness applications rely on the use of non-invasive electrodes applied on the body of a person to either inject electrical currents into the human body, e.g. transcutaneous electrical stimulation, or record biological signals, e.g. electrocardiography (ECG).

Non-invasive electrodes for transcutaneous electrical stimulation or biological signals sensing are known in the art. A comprehensive review of electrodes for transcutaneous electrical stimulation can be found in Keller and Kuhn (2008), Journal of Automatic Control 18.2 (2008): 35-45. Conventional non-invasive surface electrodes are produced either in the form of adhesive patches or in the form of electrically conductive plates that require to be fixed on the skin by means of mechanical elements, for instance medical tape.

Non-invasive electrodes have different requirements depending on their use; generally, they need to guarantee optimal application-specific performance (e.g. efficiently stimulating a muscle), while minimizing pain or skin irritation for a user.

Electrodes for transcutaneous electrical stimulation normally require good electrode-skin contact and homogenous current density at the interface with the skin. High current densities caused by electrodes with too low impedance, inhomogeneous material distributions in the electrode, or imperfect electrode-skin contact may result in loss of comfort or even pain for the user.

On the other hand, while still requiring good electrode-skin contact, electrodes for sensing applications as electroencephalography (EEG), electrocardiography (ECG) or electromyography (EMG) require low impedance with respect to the skin to detect effectively biological signals and increase the signal-to-noise ratio.

Both types of electrodes are normally placed on application-specific locations on the body and are not supposed to move during their use. Moreover, electrodes should be flexible and compliant to the movements of the user during use to avoid detachment.

Several types of electrode designs are known in the art to accomplish the aforementioned requirements for electrical stimulation or sensing, for example those disclosed in U.S. Pat. Nos. 3,998,215, 4,867,166 or 3,845,757. A problem with conventional electrodes is that certain applications, for example transcutaneous electrical stimulation, require many electrodes to be placed on the body of a user. This leads to a large amount of wiring connected to the electrodes on the user's body, thus limiting the freedom of movement of the user and reducing its comfort. Moreover, when used in proximity to joints, e.g. shoulders, traditional electrodes can easily detach.

Electrodes for ECG sensing based on liquid metal that can be "drawn" on the skin have been proposed in Yu, Zhang, and Liu (2013), Plos ONE, e58771. Unfortunately, this type of drawable electrodes are impractical to use in transcutaneous electrical stimulation applications, due to their too low impedance. Furthermore, they still require insulated wiring to connect the drawn electrodes areas on the skin with the electrical stimulator, making difficult their integration in wearable solutions.

To solve these problems, solutions embedding electrodes directly in a garment are known in the art, such as those presented in WO 2001002052, US 20130172722, or US 2012016440. However, these solutions and conventional electrodes have in common the inability of customizing the electrode shape or/and position in a fast and effective manner, which is required in certain applications, especially in clinical settings. A garment embedding electrodes that can be enabled or disabled by inserting an electrically conductive material in different embedded containers through a hole has been presented in EP 0128103. Although the garment allows to increase the conductivity of pre-defined spots on the garment, it does not allow the user to customize the shape of the electrode, but rather allows the activation of areas with predefined geometry.

Another problem of conventional electrodes is that novel neuroprosthetic devices using transcutaneous electrical stimulation may require users to wear electrodes for a prolonged time, e.g. several hours. Conventional electrodes are normally inappropriate for this usage, as they may detach or loose conductivity due to evaporation of water content in the electrode. A possible solution was offered in the invention described in WO 2012140629; however this solution still present a number of other problems highlighted above, for example the impossibility to customize electrode shape to fit user's anatomy or its use may result in discomfort upon long use, due to the presence of electrically conductive gel containers in the garment.

SUMMARY OF INVENTION

An aspect of the present invention is to provide a non-invasive "drawable" (or "paintable") electrode for transcutaneous electrical stimulation or for biological signals sensing wherein the electrically conductive area in contact with the skin can be customized by an operator such as the user him/herself or by another person. This allows to adapt the electrode shape to the anatomy of the user or to define electrodes that avoid areas of the skin where the placement of electrodes may be problematic or even harmful, for example in presence of skin ulcerations or lesions.

Another aspect of the present invention is to provide a device for easily drawing or painting the above non-invasive drawable electrode for transcutaneous electrical stimulation or for biological signals sensing on the body of a user, such as for example a marker, a syringe or a pen-like tool.

Another aspect of the present invention is to provide a non-invasive drawable electrode for transcutaneous electrical stimulation or for biological signals sensing applications, wherein a part of the electrode can be reused, for example the conductive layer (1) and non-conductive layers (2) and (7) can be washed to remove the deposed conductive material (3) and re-used.

Another aspect of the present invention is to provide a non-invasive drawable electrode for transcutaneous electrical stimulation or for biological signals sensing that can be used for several hours with no relative displacement with respect to the body due to movements of the user. The drawable electrode maintains optimal electrical contact with the skin, and thus high level of comfort by distributing uniformly electric charge on the skin, even in presence of skin imperfections Another aspect of the present invention is to provide a non-invasive drawable electrode for transcutaneous electrical stimulation or for biological signals sensing which allows to insulate a deposed conductive material from unintentional contact with external objects or other body parts.

Another aspect of the present invention is to provide a non-invasive drawable electrode for transcutaneous electrical stimulation or for biological signals sensing where the insulation of the deposed conductive material can be induced by a user in relatively short time, e.g. minutes.

Another aspect of the present invention is to provide a non-invasive drawable electrode for transcutaneous electrical stimulation or for biological signals sensing that can possibly deliver drugs during the use of the electrode.

A final aspect of the present invention is to enable novel applications based on biological signal sensing or transcutaneous electrical stimulation that require multiple electrodes.

All these aspects are achieved by a device and a system comprising the features described in the claims.

It is therefore an object of the present invention to provide for a non-invasive electrode for use in transcutaneous electrical stimulation or biological signal sensing comprising:
  i. an electrically conductive layer (1) operatively connectable with means for delivering electrical current and/or sensing electrical signals (9), said conductive layer (1) being adapted for delivering electrical current or sensing electrical signals, and having an upper face and a bottom face; and
  ii. an electrically insulating element (2) designed to contact the skin and at least a portion of the electrically conductive layer (1) so to maintain said electrically conductive layer (1) separated from the skin
wherein said conductive layer (1) and said insulating element (2) are pervious in a way as it can be penetrated and/or crossed up to the skin surface by an electrically conductive material (3) applied on the upper face of the conductive layer (1) and/or the insulating element (2).

In one embodiment, the electrode further comprises an additional electrically insulating layer (7) designed to at least partially cover the upper face of the conductive layer (1).

In a preferred embodiment, the insulating layer (7) is pervious in a way as to be penetrated and/or crossed by an electrically conductive material (3) applied thereon.

In one embodiment, the electrode is incorporated in a garment.

In one embodiment, the electrode further comprises at least a conductor (6) operatively connected with the electrically conductive layer (1) and operatively connectable with means for delivering electrical current and/or sensing electrical signals (9).

In a preferred embodiment, the conductive material (3) used is in liquid or gel form.

In a particular embodiment, the conductive material (3) further comprises additives for optimizing, depending on an user's need, the electrical conductivity thereof and/or mechanical adhesion between the electrode parts penetrated and/or crossed by the conductive material (3) and the skin.

In a particular embodiment, the conductive material (3) is characterized by the fact that the physical state of its surface not in contact with the skin may be modified to such an extent that a solid outer-shell is created.

In another embodiment, the physical state of the surface of the conductive material (3) is modified via heat exchange, light drying, photopolymerization, oxydation and/or evaporation of a liquid phase comprised within the conductive material (3).

In another embodiment, the conductive material (3) comprises a radical initiator that, upon induction of a photo-, thermo- or chemical-activation, promotes a radical polymerization of the conductive material's surface not in contact with the skin.

In one embodiment, the conductive material (3) is characterized by the fact that it comprises one or more chemical compounds and/or medicinal products.

In a particular embodiment, the conductor (6) consists at least in part of the conductive material (3).

Another object of the invention relates to a system comprising several electrodes as previously defined, characterized by the fact that it uses the same electrically insulating element (2) for all the electrodes.

A further object of the invention relates to a garment comprising the above described electrodes or system.

supporting the conductive layer (1). In this case the non-conductive part (2) also insulates the conductive layer (1) from external contact with the conductive layer (1).

Figure 5:
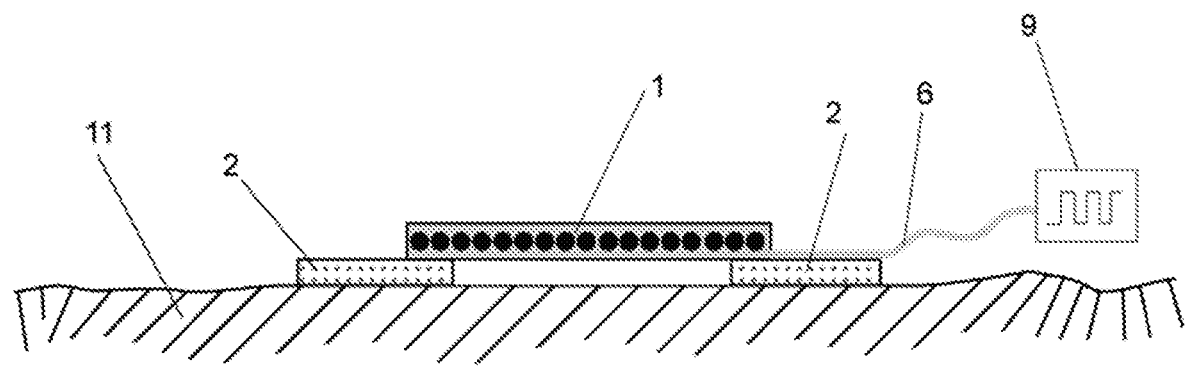

FIG. 5 shows a further embodiment of the invention wherein the non-invasive drawable electrode comprises two electrically insulating elements (2) shaped as spacers to separate the electrically conductive layer (1) from the skin.

Figure 2:
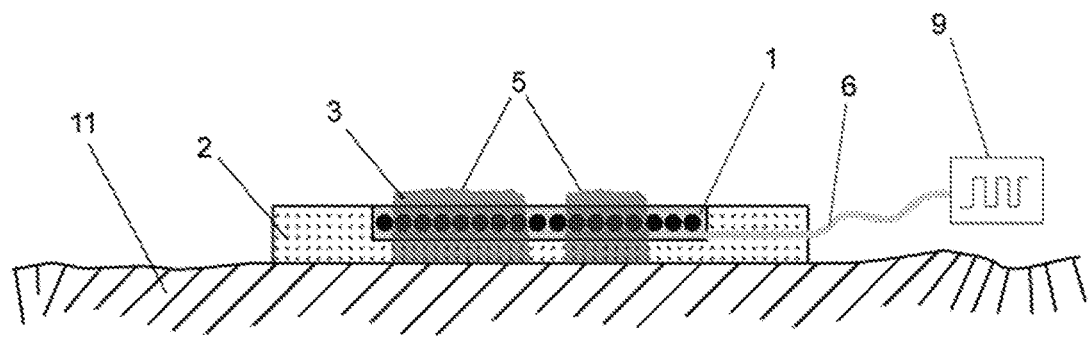
FIG. 2 shows another embodiment of the invention wherein the non-invasive drawable electrode of FIG. 1 further comprising a conductive material (3) that creates an electrical contact between the electrically conductive layer (1) and the skin (11) in desired areas (5). Said desired areas (5) can be of custom shapes, as the conductive material (3) can be precisely deposed on the electrically conductive layer (1). The result is a non-invasive drawable electrode with customizable electrically conductive areas.
Figure 6:
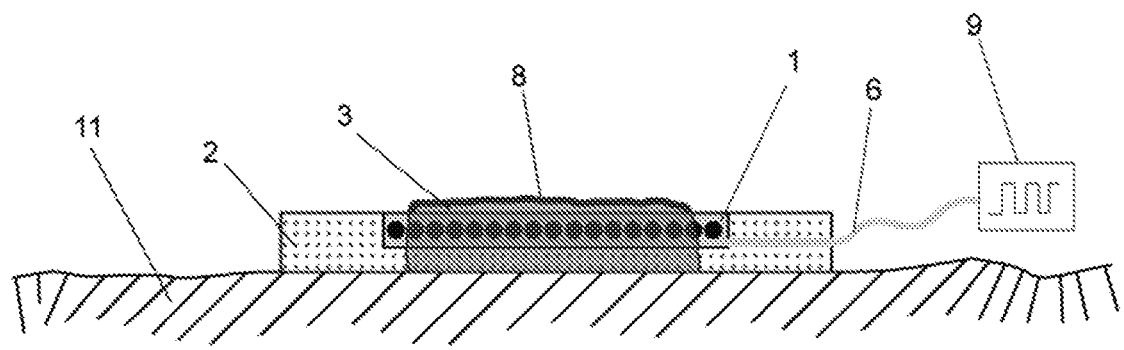

FIG. 6 shows an embodiment of the invention wherein the non-invasive drawable electrode of FIG. 2 comprises a fluid conductive material (3) having a solid, dry and insulating outer shell (8) as to protect the underlying liquid and conductive bulk, ensuring safety and comfort.

Figure 7:
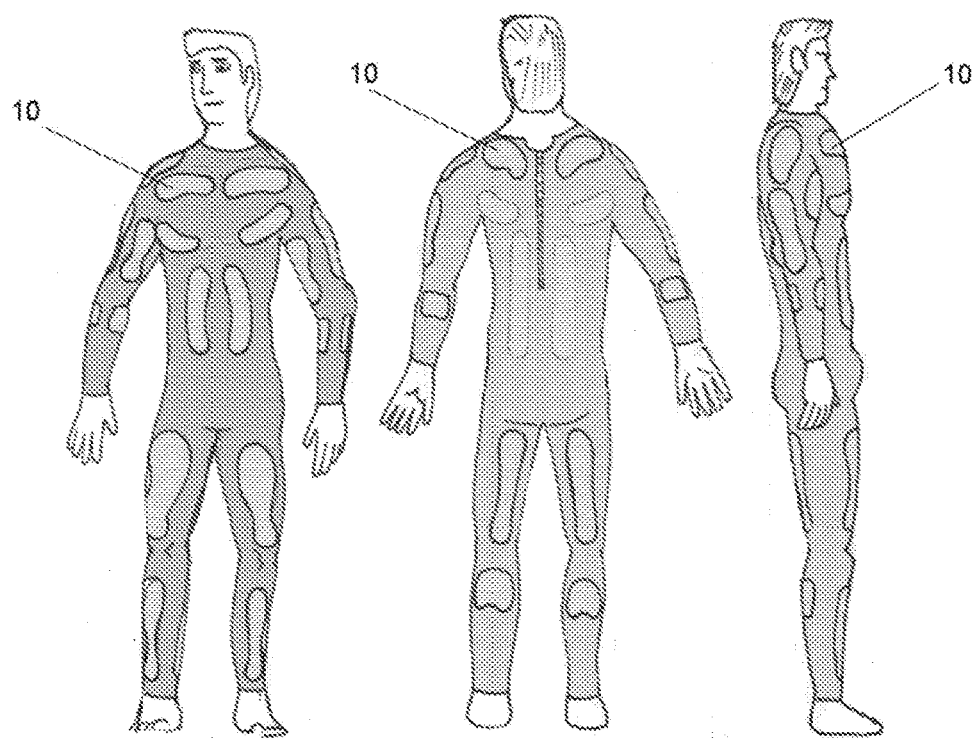

FIG. 7 shows a full body garment integrating a plurality of drawable electrodes of the invention all over the body. Said garment embeds several drawable areas (10) over relevant areas of the body.

Figure 8:
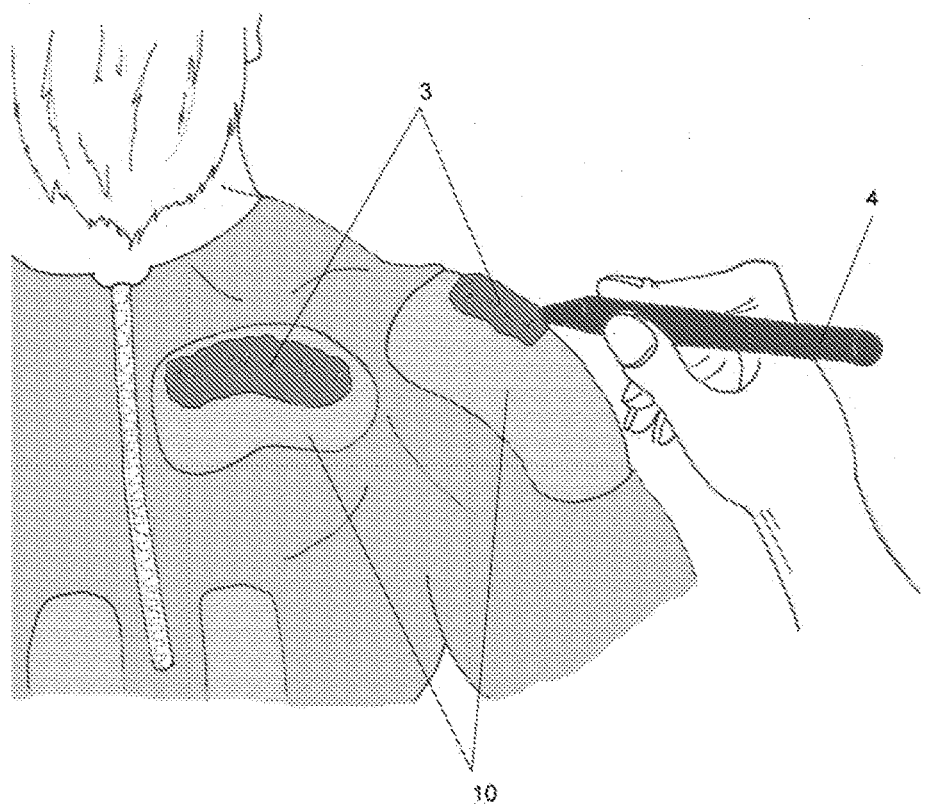

FIG. 8 shows an example of "electrode drawing" by deposition of the conductive material (3) on drawable areas (10) using a delivery system (4)—in this case a pencil-like instrument. Wiring (6) that connect the conductive layer in the garment to an electrical stimulator or sensing device (9) are embedded into the garment and not shown in the drawing.

Figure 9:
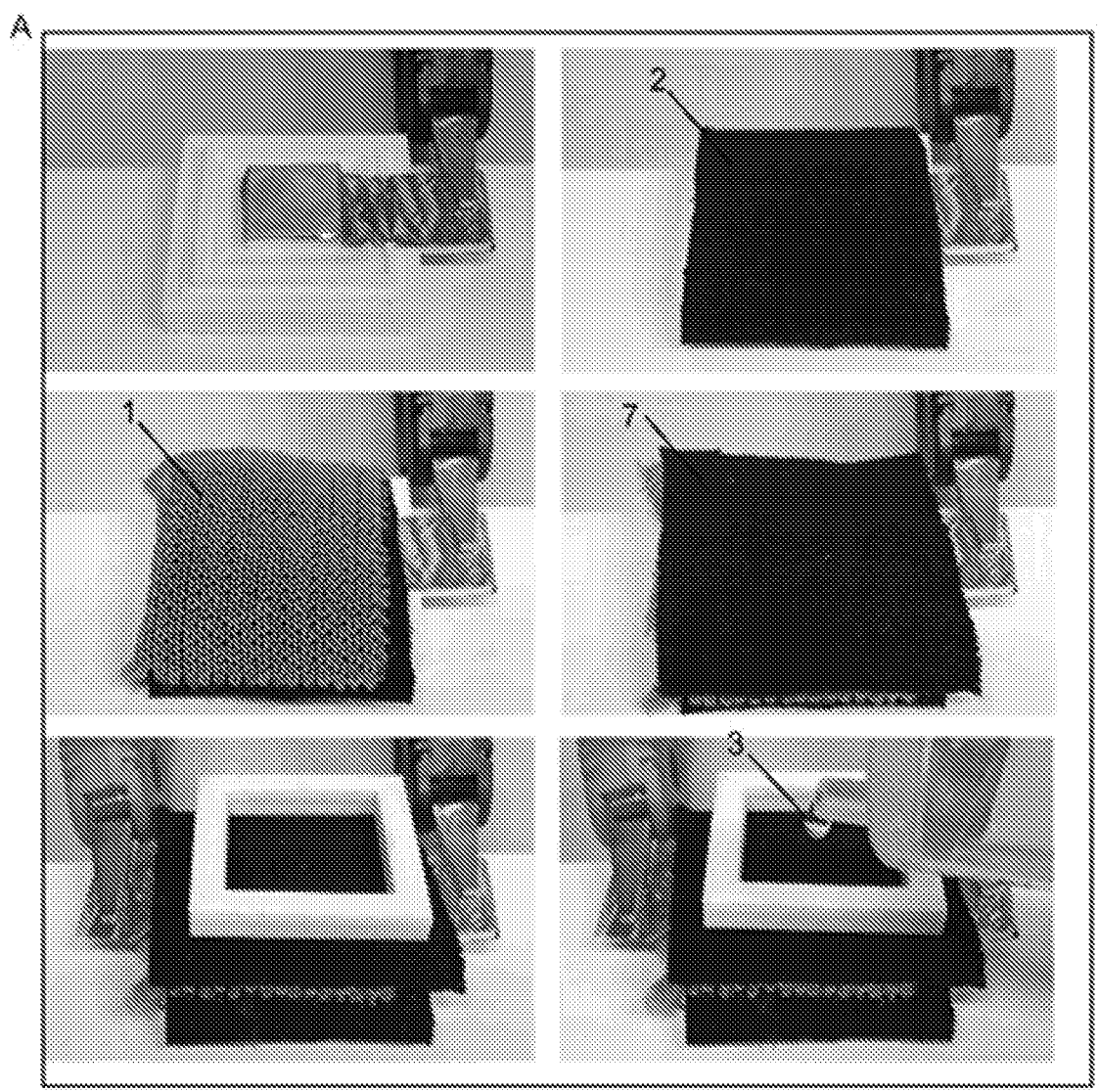

FIG. 9 A) Setup for characterizing the impedance of a drawable electrode. A conductive layer (1) is sandwiched between two non-conductive layers (2) and (7). After the application of a conductive material (3), the impedance between two copper contacts is characterized using an LCR meter.

B) Impedance response of a sample of a drawable electrode after the application of the conductive material (3).

C) Impedance over time after application of the conductive material (3) on two different types of drawable electrodes, repeated over three different samples, at a frequency of 10 KHz.

Figure 10:
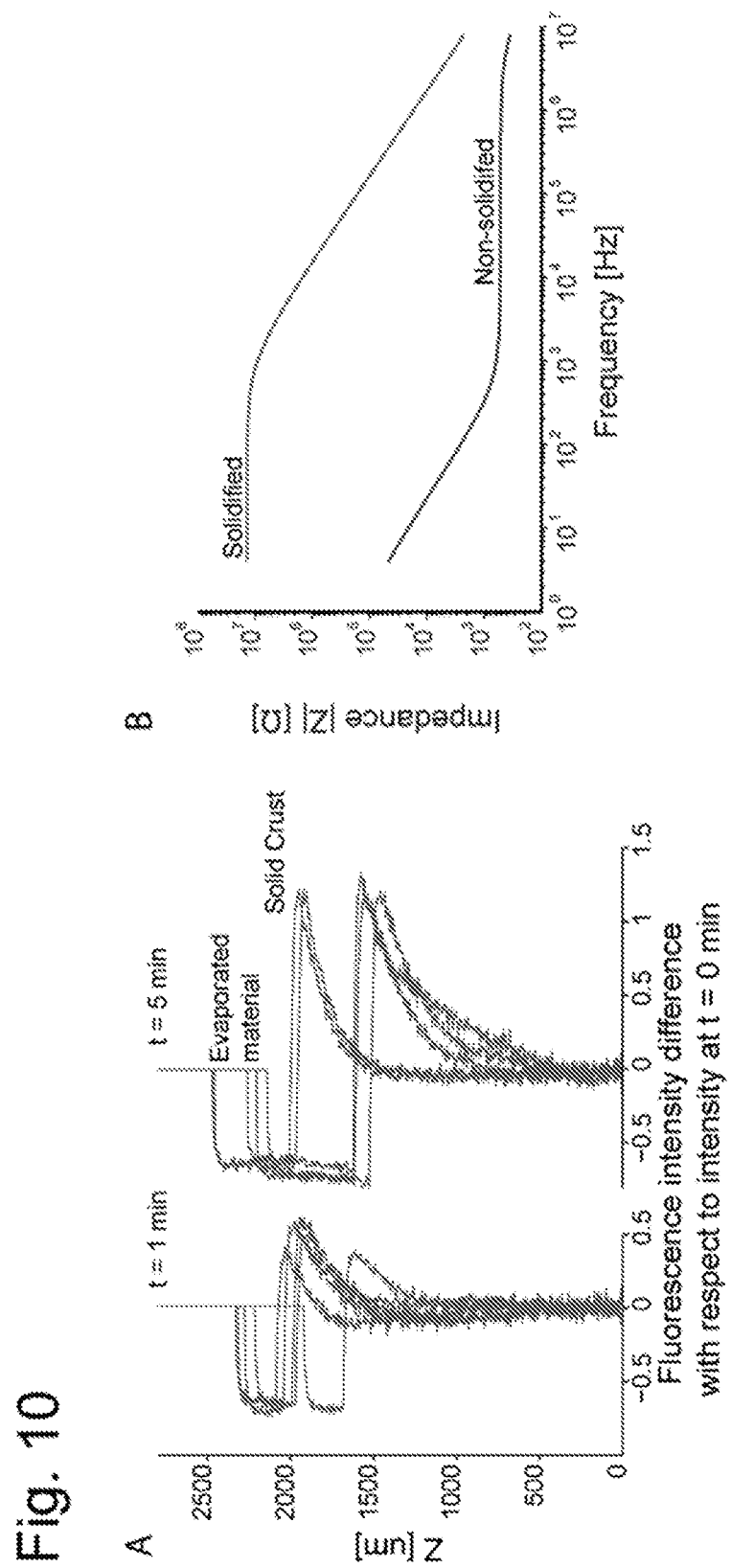

FIG. 10 A) Variation of fluorescence intensity across the depth of a sample of conductive material (3) measured using confocal microscopy. The material was deposed in a cover slide with wells. Z-depth of 0 in the figure indicates the material in contact with the bottom of the well, i.e. the cover slide, whereas a positive Z value indicates the distance of the material from the bottom of the well. The upper surface of the sample in contact with the air was exposed to a heating airflow normal to the surface for 1 and 5 minutes. Densification of a solid crust is visible due to variation in auto-fluorescence of the conductive material in function of the quantity of solvent present in it.

B) Impedance of the conductive material (3) when liquid and solidified.

Figure 11:
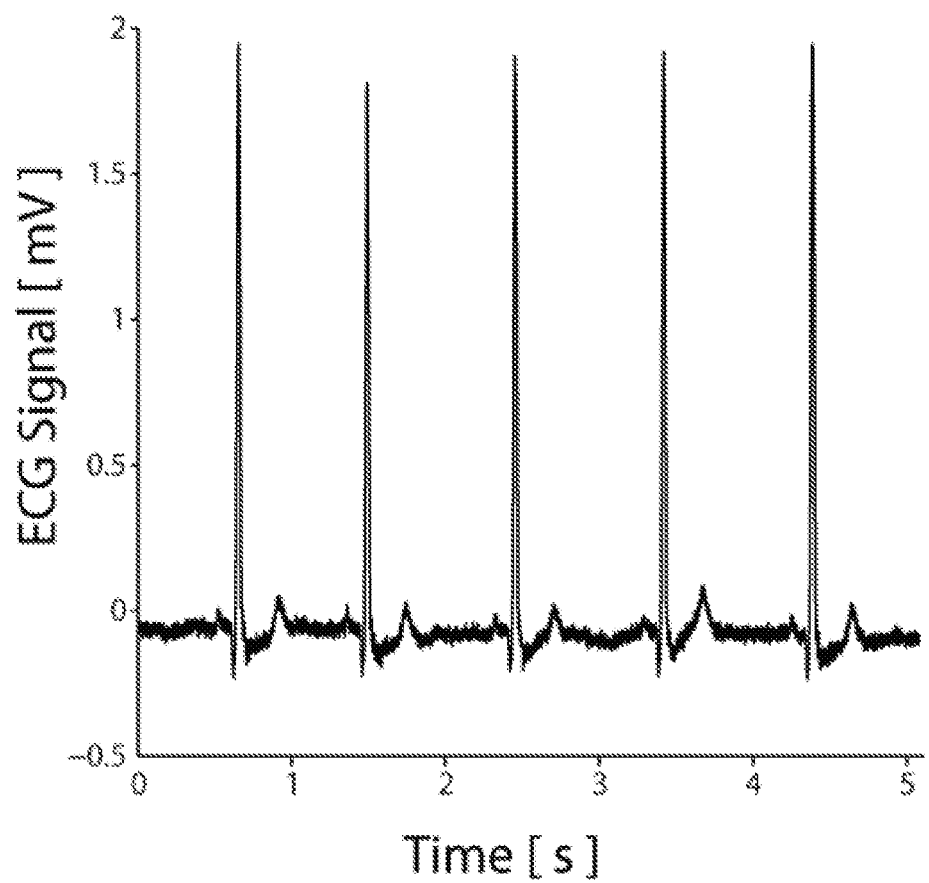

FIG. 11 shows an ECG signal acquired from a drawable electrode placed on the chest in proximity of the heart.

DESCRIPTION OF EMBODIMENTS

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a conductive material" includes a plurality of such conductive materials.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

In all the following figures the skin of the user (or another biological tissue) to which the electrode is applied is indicated with the label (11).

Figure 1:
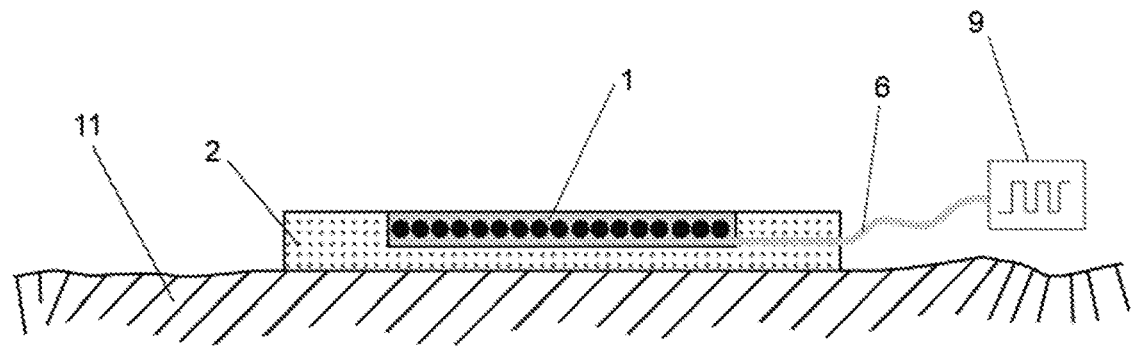
FIG. 1 shows an embodiment of the non-invasive drawable electrode for transcutaneous electrical stimulation or biological signal sensing of the invention, comprising a pervious electrically conductive layer (1) for delivering electrical current or sensing biological signals, and one electrically insulating element (2) for maintaining said electrically conductive layer (1) separated from the skin (11). The electrically conductive layer (1) can be electrically connected through e.g. wirings (6) to an external device (9) for transcutaneous electrical stimulation or biological signal sensing, such as a neuromuscular electrical stimulator or an EEG/EMG/ECG acquisition system, depending on the application of interest.

As shown in the embodiment depicted in FIG. 1, the electrode of the invention comprises an electrically insulating element (2) in contact with the skin and an electrically conductive layer (1) fixed on top of the electrically insulating element (2).

As used herein, the term "electrode" refers to an element used to connect an electric circuit with the skin. An electrode is generally a metallic element that conducts an electric current toward or away from an electric circuit, said circuit being composed in its simplest embodiment of two electrodes and a material as a dielectric, an electrolyte, or a semiconductor placed in between. In this context, an "electrically conductive layer" refers herein to the portion of the electrode which is responsible of the delivery of an electrical current from or to a conductor, operatively connected to an external device such as an electrical stimulator, to or from the skin.

The electrically conductive layer (1) has an upper face and a bottom face, and can be shaped to have any size and any form, such as for instance a plate or a pad, depending on the user's needs, on the areas to be electrically stimulated/sensed and the like. The electrically conductive layer (1) can be made of any suitable electrical conductive material, including but not limited to metals such as Au, Pt, Al, Cu and the like, as well as any alloy thereof and combinations thereof, conductive polymeric materials, composite material such as polymeric materials embedding metal particles and/or metal strands or stripes, including insulating materials functionalized with electrically conductive elements, patterns or fibers, for example carbon-filled polymers, electrically conductive inks, printed circuits boards and the like, as well as any suitable combination thereof.

As used herein, a "polymeric material" is any material comprising polymers, i.e. molecules composed of many repeated smaller units, or subunits, called monomers, usually bound through covalent bonds. The polymeric material can be a linear polymer consisting of a long linear chain of monomers, a branched polymer having a long backbone chain with several short side-chain branches covalently attached, a cross-linked polymer having monomers of one long or short chain covalently bonded with monomers of another short or long chain and the like. Polymers can be homopolymers (having monomers of the same type), random or alternating copolymers (having different repeating units) and/or graft copolymers consisting of a chain made from one type of monomer with branches of another type. Polymers can also be elastomers (also called rubbers), lightly cross-linked networks, or thermosets, densely cross-linked networks. Rubbers are characterised by the property of high elasticity, i.e. elastic behaviour at high stresses and strains. Polymer materials may also be formed by blending two or more polymers into physical mixtures.

The electrically conductive layer (1) can be substantially made for example, but not limited to, of electrically conductive and stretchable fabrics and/or polymers, such as knitted fabric comprising or consisting of electrically conductive materials such as copper wires meshes or other electrically conductive materials. The electrically conductive layer can also be made by a fabric coated or plated by an electrically conductive material such as "Silver plated 76% Nylon 24% elastic fiber fabric" from "Less EMF Inc." or materials integrating electrically conductive fibers made in silver, or stainless steel, or other conductive materials, such as "Nm 10/3 electrically conductive yarn, 80% polyester 20% stainless steel" from "Plug&Wear, plugandwear.com".

The electrically conductive layer (1) is fixed laterally, on top and/or below of an electrically insulating element (2) in direct contact with the skin. For "electrically insulating element" is herein meant a portion of the electrode acting as an electrical insulator, that is, an electrode's element that avoids or limits as far as possible the conduction of an electric current from the electrically conductive layer (1) to the skin.

Generally speaking, an electrically insulating element is substantially composed of a material whose low conductivity make the flow of current through it negligible. In the embodiment shown in FIG. 1, for instance, the electrically insulating element (2) can have an extension greater or equal to the electrically conductive layer (1) and, being placed in direct contact with the bottom face of the conductive layer, prevents any electrical contact between the skin and the electrically conductive layer (1) due to its material's nature.

The electrically insulating element (2) can be substantially made of any suitable insulating material such as for example, but not limited to, electrically insulating and stretchable fabric and/or polymers such as textiles derived from polyesther-polyurethane-copolymer, like Spandex, Lycra, Elastane, fiberglass woven fabric, knitted rubbers, glass wool, polyethylene woven fabric, polyesters such as polyethylene terephthalate (PET), latex, nylon, polytetrafluoroethylene (PTFE), silicon and the like, as well as by coating fabric comprising thereof.

Moreover, the electrically insulating elements (2), can be made for example of an electrically insulating material that can tolerate mechanical deformations caused by movements, muscle contractions, and other geometrical changes. For example, but not limited to, said electrically insulating elements (2) for supporting the electrically conductive layer (1) can be made of polymeric materials such as Acrylonitrile butadiene styrene (ABS), poly ethylene (PE), poly propylene (PP), rubbers, polyesthers, epoxys or any suitable combination thereof.

However, additionally or alternatively to the properties of the material composing the insulating element, the design of this latter can also play a role in the electrical insulation between the conductive layer and the skin. For example, in the embodiment of the invention shown in FIG. 4, an electrically conductive layer (1) is kept at distance from the skin through an electrically insulating element (2) supporting the conductive layer (1). Furthermore, in this case the non-conductive part (2) also insulates the conductive layer (1) from external environment. In still another embodiment shown in FIG. 5, at least two or even more electrically insulating elements (2) can be shaped and/or positioned as spacers so to separate the electrically conductive layer (1) from the skin. In these two cases, an empty space between the conductive layer and the skin is used, the facto, as the insulating component of the electrode; such empty spaces can also be studied in advance so to have desired areas (5) of electrical contact, as will be detailed later. As it will be evident for a person skilled in the art, any kind of format can be envisaged as long as the electrically insulating element(s) acts as impeding means for the conductive layer/skin contact.

The electrically insulating elements (2) and the electrically conductive layer (1) can be fixed together by any method. For example, they can be sewed together, glued together, weaved as one unique fabric, the electrically conductive layer (1) can be printed on said electrically insulating support (2) through photolithographic techniques, or can be directly fixed or embedded in the electrically insulating element (2) as long as the insulating function of the electrically insulating element (2) is not compromised.

The electrically conductive layer (1) are designed to be electrically operatively connectable through e.g. wirings (6) to an external device (9) for delivering an electrical current (e.g. for transcutaneous electrical stimulation) and/or fir biological signal sensing, such as a neuromuscular electrical stimulator or a biological signal acquisition system (e.g. that can acquire for example EEG, EMG, or ECG signals), depending on the application of interest. The electrically conductive layer (1) can be easily connected to an external device (9) by e.g. plugging a wire (6) into a plug portion of the electrode operatively connected to the electrically conductive layer (1). Additionally or alternatively, the electrode can already comprise in its design one or more wiring conductors (6) operatively connectable (e.g. pluggable) to an external device (9). The conductors (6) can have any suitable shape and size, and can be made or can comprise the same electrical conductive materials already specified for the electrically conductive layer (1).

For the sake of clarity, in the frame of the present disclosure, the expression "operatively connected" or "operatively connectable" reflects a functional relationship between the several components of the electrode, a system comprising several electrodes and/or an external device among them, that is, the expression means that the components are correlated in a way to perform a designated function. The "designated function" can change depending on the different components involved in the connection; for instance, the designated function of an electrically conductive layer of the electrodes of the invention operatively connected to a device such as a transcutaneous electrical stimulation and/or biological signal acquisition system is the delivery in either way of an electrical current. The same can be said for instance for the conductor (6) according to the invention. A person skilled in the art would easily understand and figure out what are the designated functions of each and every component of the system of the invention, as well as their correlations, on the basis of the present disclosure.

Figure 3:
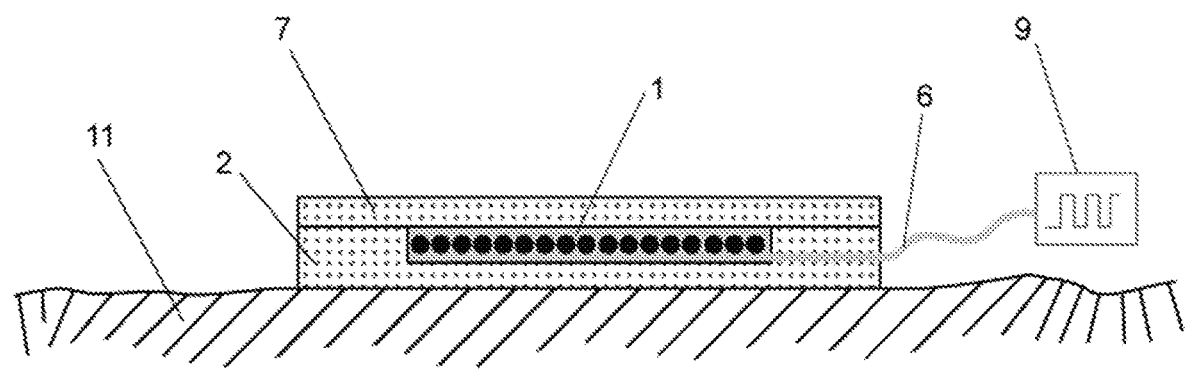
FIG. 3 shows a further embodiment of the invention wherein the non-invasive drawable electrode of FIG. 1 has an additional insulating layer or coating (7) to prevent undesired electrical short-circuits or interferences of the electrically conductive layer (1) with objects in proximity, such as other body parts coming in contact with the electrically conductive layer (1) or clothes worn on top of the electrode.

In another embodiment of the present invention, such as the one shown in FIG. 3, the electrically conductive layer (1) can be insulated by an additional insulating layer or coating (7) to prevent undesired electrical short-circuits or interferences with objects in close proximity, such as other body parts coming in contact with the electrically conductive layer (1) or clothes worn on top of the electrodes. This additional insulating layer (7) may cover partially or entirely the underlying electrically conductive layer (1). Alike the embodiment presented in FIG. 1 or 2, a conductive material (3) can be deposed on the electrically conductive layer (1), in this case on its additional insulating layer (7), to define desired electrically conductive areas (5) that connects the electrically conductive layer (1) with the skin.

The insulating layer (7) has substantially the same characteristics of the electrically insulating element (2) of the electrode of the invention previously described, either in terms of materials, structure (e.g. permeability) and/or design. However, in preferred embodiments of the invention, the insulating layer (7) covers and insulates the entire upper face of an electrically conductive layer (1). Moreover, in preferred embodiments, the insulating layer (7) is pervious, as will be detailed in the next paragraph.

One of the key features of the electrically conductive layer (1) of the electrode of the invention and, in some embodiments, of the electrically insulating element (2) and/or the electrically insulating layer (7), relies in its (their) physical structure. Actually, said electrode element(s) has (have) such a pervious structure in a way as it can be penetrated and/or crossed up to the skin surface by an electrically conductive material (3) applied on the upper face of the conductive layer (1) and/or on the insulating element (2) and/or the insulating layer (7). For "pervious" is herein meant the structural characteristics of one or many electrode portions of the invention that render such portion(s) permeable to the passage of the above-cited electrically conductive material through it (them). In particular, a pervious (either conductive or insulating) portion of the electrode comprises a network or mesh of the material(s) composing said electrode's portion interspaced by empty spaces that permit the physical passage of the conductive material once applied thereon. Such a structure geometry is also advantageous in terms of adaptability of the electrode's portion(s) to mechanical deformations such as user's movements, user's body surface, muscle contraction and so forth, while maintaining at the same time an excellent electrical conductivity and body adhesion.

As briefly mentioned above, the electrical contact between the electrically conductive layer (1) and the skin can be obtained through a conductive material (3) deposed on top of the electrically conductive layer (1) in desired areas (5) as shown in FIG. 2. As used herein, an "electrically conductive material" is any suitable material able to penetrate through the pervious layers composing the electrode of the invention and to create an electrical connection between the electrically conductive layer (1) and the skin.

In the configuration shown in FIG. 1, no direct electrical connection exists between the electrically conductive layer (1) and the skin, thus no sensing nor stimulation can be performed. However, as shown in FIG. 2, once a conductive material is applied over the electrically conductive layer (1) and, in the depicted case, the electrically insulating element (2), it seeps through said electrode portion(s) up to the skin.

A "desired area" is a portion of the skin that needs to be electrically stimulated and/or electrically sensed. Said desired areas (5) can be of custom shapes. The conductive material (3) penetrates the volume of the electrically insulating element (2) and electrically conductive layer (1) underneath the desired areas (5) where the conductive material (3) has been deposed, and electrically connects the electrically conductive layer (1) and the skin. The conductive material (3) can be dispensed on the electrically conductive layer (1) by using a device that allows precise deposition on the desired areas (5), for example by means of a syringe, stamp- or pencil-like instrument. The result is a non-invasive drawable electrode with easily customizable electrically conductive areas.

Figure 4:
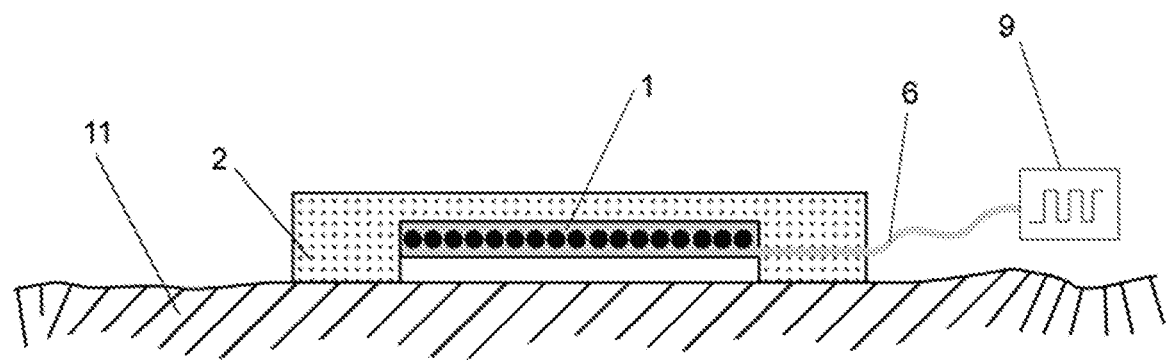
FIG. 4 shows a further embodiment of the invention wherein the non-invasive drawable electrode comprises an electrically conductive layer (1) kept at distance from the skin (11) through an electrically insulating element (2)

The definition of desired electrically conductive areas (5) in e.g. the embodiments presented in FIG. 4 and FIG. 5 can be performed in two ways. First, as already explained, the conductive material (3) can be deposed on top of the electrically conductive layer (1). Additionally or alternatively, the conductive material (3) can be deposed directly on the skin and successively the ensemble comprising the electrically conductive layer (1) and the supporting electrically insulating elements (2) can be overlaid to the deposed conductive material (3).

The conductive material (3) can for instance consist of or comprise conductive wires able to penetrate the pervious layers of the electrode, a thin powder able to leach through the pervious layers of the electrode (i.e. the particles' size must be smaller than the empty spaces of the pervious layers of the electrodes) or, in preferred embodiments, a liquid or a gel, as well as any suitable combination thereof. Metals such as Au, Pt, Al, Cu and the like, as well as any alloy thereof and combinations thereof, conductive polymeric materials, composite material such as polymeric materials embedding metal particles and/or metal strands, including insulating materials functionalized with electrically conductive elements, carbon-filled polymers, electrically conductive inks and the like can be part of, or can substantially compose, for instance a thin powder, a liquid or a gel.

As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

In some embodiments, the gel can be a hydrogel. The term "hydrogel" refers to a gel in which the swelling agent is water. A hydrogel is a macromolecular polymer gel constructed of a network of cross-linked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties. Furthermore, hydrogels permit diffusion of e.g. aqueous compositions therethrough, and have a high permeability to water and water-soluble substances, such as nutrients, metabolites, drugs and the like.

Some examples of hydrogels include, but are not limited to, synthetic or natural polymeric hydrogel, such as those consisting of or comprising polysaccharides, co-polymers of polysaccharides (cellulose, agarose, alginate, starch, chitosan and many others), polypeptides (silk, collagen, gelatin and many others), amelogenin and the like.

Several physical and chemical properties of the gels, hydrogels and liquids are dependent upon concentration. Increase in hydrogel concentration may change the gel pore radius, morphology, or its permeability, as well as, most importantly, its viscosity and its conductivity. One skilled in the art will appreciate that the various parameters of a liquid or gel for use as an electrically conductive material can be selected based on the user's needs, such as e.g. the needed conductivity or the size of a desired area (5). The mechanical properties of the material can be tailored by e.g. changing the (hydro)gel (molecular chain length, crosslinking, water content and so forth) and/or its composition or constituents.

In preferred embodiments of the invention, therefore, in order to facilitate the deposition of the conductive material (3) in the desired areas (5), its viscosity should range from liquid to gels. For example, the conductive material (3) can consist or comprise water-soluble polymers with adhesive properties, such as Polyvinylpyrrolidone (PVP) also known as Luvitec® from BASF, dissolved in a solvent such as water, ethanol or isopropyl alcohol, or a mixture of more solvents. Furthermore, the electrical conductivity of the conductive material (3) might be required to be optimized according to the application, for example when low impedance is required during biological signals sensing and relatively lower conductivity is required during transcutaneous electrical stimulation. To this aim additives, fillers or dispersions of solid microparticles or ionic compounds such as sodium chloride, metallic micro and nanoparticles, metallic salts, carbon nanotubes, conductive nano-rods and so forth can be added to the conductive material (3) to adjust its electrical conductivity.

An example of a drawable electrode is shown in FIG. 9A. A conductive layer (1) made of a mesh of stainless steel wires (80 μm diameter) knitted in polyester is inserted between two non-conductive layers made of polyester (2) and (7).

To electrically characterize the drawable electrode, the lower layer (2), which is normally in contact with the skin, is deposed on top of a squared copper electrode (1.2 cm×1.2 cm), connected to a probe of an LCR meter (HIOKI 3536). The conductive layer (1) is also connected to a second probe of the LCR meter using another copper contact. The conductive material (3), made of the conductive polymer polyvynylpyrrolidone (PVP), mixed with water, is deposed on top of the outer non-conductive layer (7), and penetrates the three layers (7), (1) and (2), connecting the copper electrode plates, representing the skin in normal operating conditions, with the conductive layer (1). The impedance of the drawable electrode is characterized at different frequencies in the range 10 Hz-1MHz.

FIG. 9B shows the module of the impedance of the drawable electrode after application of the conductive material (3). The electrical connection between the conductive layer (1) and the copper electrode through the non-conductive layer (2) is clearly present after the application of the conductive material. The impedance curve before the application of the material is not shown, having a resistance above 10 MΩ, thus demonstrating the effectiveness of the non-conductive layer (2). The resistivity ρ of the non-conductive layer (2) soaked with the conductive material (3) was computed considering the area of the copper electrode contact (1.2 cm×1.2 cm) and the thickness of the fabrics used for the non-conductive layer (2), I=0.45 mm, following $\rho(f)=R(f) A/I$.

FIG. 9C shows the mean module of the impedance (upper line) and standard deviation at 10 KHz after N=1, 2, 5, 10, 30, 60, and 120 minutes from the application of the conductive material, repeated on three samples. After 2 hours from application, measured resistivity is ρ=80 Ω·m, still acceptable for a non-invasive electrode (e.g. state-of-the-art Compex electrodes have resistivity around 100 Ω·m, according to measurements performed in Lawrence, Marc. (2009), Transcutaneous electrode technology for neuroprostheses. Zürich: ETH). FIG. 9C shows also the mean impedance and standard deviation of a drawable electrode (bottom line) made with a more conductive textile (Silver plated 90% Nylon 8% Dorlastan from Plug&Wear, plugandwear.com) for the conductive layer (1).

In addition, some applications might require the conductive material (3) to attract water molecules from its surroundings, for example to maintain the desired electrical conductivity for long durations or absorb sweat or wounds exudate. To do so, in some embodiments the conductive material (3) can include humectants, for example polyethylene glycol (PEG), to tailor its hygroscopicity to the need of the application.

In some embodiments of the invention, the conductive material (3) can also be used as a vector of chemical compounds or medicinal products, thus allowing the combination of electrical stimulation and/or sensing to skin surface during drug delivery or iontophoresis. Chemical compounds or medicinal products can include but are not limited to, for example, emollients, anti-pruritics (Antihistamines, Corticosteroids, Local anesthetics, Counterirritants), antifungals, disinfectants, scabicides, pediculicides, tar products, vitamin A derivatives, vitamin D analogues, keratolytics, abrasives, systemic antibiotics, topical antibiotics, hormones, desloughing agents, exudate absorbents, fibrinolytics, proteolytics, sunscreens, antiperspirants, immune modulators, antimetabolites and/or other chemotherapy drugs.

Other embodiments using a liquid or gel conductive material (3) might require that its external surface is not liquid/gel nor conductive, as to protect the underlying liquid and conductive bulk, ensuring safety and comfort. For this aim, a surface hardening of the conductive material (3) can be obtained, for example by evaporation of the solvent, leading to a dry and electrically insulating outer shell (8), as shown in FIG. 6. A possible composition of said conductive material (3) can be a solution comprising 33% wt of Polyvinylpyrrolidone (PVP) K 60, Mr~160000, 34% $H_2O$, 33% wt isopropyl alcohol, and the densification of the outer shell (8) may be induced by solvent evaporation through convection and light drying, for example using a hairdryer device.

In some embodiments of the invention, the conductive material (3) can also include a photo-initiator, for example any compound from the Irgacur® or Darocur® product family, such that the densification of the surface can be obtained, for example by a polymerization process provoked by visible, infra-red or ultraviolet light (photo-polymerization). In other embodiments of the invention, said conductive material (3) can also include a radical initiator, for example any compound from the Irgacur® or Darocur® product family, such that the densification of the surface can be obtained for example by thermal activation or chemical induced radical polymerization.

FIG. 10A shows the formation of a hardened, denser surface of the conductive material (3), made of a solution of PVP and water, after exposition to a conventional hair-dryer for 1 or 5 minutes. The figure shows the difference of the fluorescence intensity before and after hair drying a sample of the conductive material using an air flow of 80° C. and 15 m/s (3). The conductive material (3) was deposed in a cover slide with wells. A Z-depth of 0 in the figure indicates the material in contact with the bottom of the well, i.e. the cover slide, whereas a positive Z value indicates the distance of the material from the bottom of the well. The upper surface of the sample in contact with the air was exposed to a heating airflow normal to the surface for 1 and 5 minutes. Fluorescence intensity profiles were obtained with confocal microscopy techniques, using excitation wavelength of 480 nm and recording its autofluorescent emission at wavelength ranging from 515 to 560 nm. The autofluorescent signal is function of the ratio polymer/solvent present in the conductive material (3) where a higher fluorescence indicates higher ratio polymer/solvent. Evaporation of part of the material after hair drying is clearly visible, as well as the formation of a crust at the interface of the conductive material (3) with the air.

FIG. 10B shows the electrical impedance of the same solution of conductive material in its liquid and solidified state. The conductive material (3) shows higher impedance after solidification.

Drawable electrodes are not only useful in transcutaneous electrical stimulation settings but as well in biological signal sensing scenarios. FIG. 11 shows an ECG signal recorded using a drawable electrode placed on the chest of a subject. The drawable electrode was connected to a biosignal data acquisition system (gUSBamp, g.tec Medical Engineering GMBH).

The embodiments of non-invasive drawable electrodes described so far, including those presented in FIGS. 1 to 6, can be further implemented in a system comprising a plurality of electrodes, where two or more electrodes may share the same electrically insulating element (2), depending on the application. Said system allows the user to paint multiple electrodes of desired shapes and positions. The electrodes comprising the system can be connected between each other or to an instrument for electrical stimulation or biological signals recording. The electrically insulating element (2) can be made of a wearable item such as a garment, cast, bandage, compression garment, orthoses and/or exoskeleton. For example, FIG. 7 shows one elastic, pervious, and insulating full body garment, comprising several distinct drawable areas (10) comprising the electrode previously disclosed. A user can fabricate electrodes of custom shapes by deposing or "drawing" the conductive material (3) on top of an electrically conductive layer (1), exposed in the drawable areas (10). The act of electrode fabrication by "drawing" or "painting"—i.e. by deposing conductive material (3)—is shown in FIG. 8.

In a very particular embodiment of the invention, the conductor (6) consists at least in part of the conductive material (3). This is particularly advantageous in the case said conductive material (3) is in a liquid or a gel form. Once poured onto the various electrode layers into desired areas (5), the liquid or gel conductive material (3) could also be poured into or onto ad-hoc, non-porous portions of e.g. the insulating layer (7) placed on the conductive layer (1). Alternatively or additionally, fillable tubular elements, chambers and the like can be operatively connected to any suitable portion of the electrode and could also possibly be used as disposing elements for the conductive material (3) on the desired areas (5). Wirings conductors (6), even stemming directly from an external device (9) or forming part of an all-in-one wiring system that could be for instance included in a garment, can be implicated in the final functional electrical connection.

To facilitate the identification of body locations that are needed to provide a defined function, for example to generate or sense the activation of a specific muscle, drawable areas (10) can be distinguished by colours, symbols, numbers, words or other markers. Moreover, according to the application, the wearable item can for example be made or can comprise compressive fabric, can include elastic silicon gripper bands or can even have a rigid shape in order to provide comfort and stable positioning of the electrodes on the body during the use.

These embodiments including multiple non-invasive "drawable electrodes" can have several applications, for example but not limited to:

electrical stimulation and/or biological signals sensing in physical and occupational therapy, also including chemical compounds delivery for treating spasticity, pain, skin diseases and the like;

electrical stimulation and/or biological signals sensing in severe burn and surgery, also including chemical compounds delivery to promote tissue regeneration and reduce pain;

electrical stimulation and/or biological signals sensing in sportive training and/or aesthetics;

any application that might require electrical stimulation of tissues and/or biological signals sensing to and from a collection of points of the body defined by the user that requires stable electrode positioning and that may require chemical compounds delivery during sensing and/or stimulation.

The invention claimed is:

1. A non-invasive electrode for transcutaneous electrical stimulation or biological signal sensing of a user, the electrode comprising:
   an electrically conductive layer operatively connectable to a device for at least one of delivering electrical current and sensing electrical signals, the electrically conductive layer configured to deliver an electrical current or sensing electrical signals, and having an upper face and a bottom face, the non-invasive electrode is adapted to be worn by the user such that an area of the upper face is exposed to an exterior environment for manual application of electrically conductive material; and
   an electrically insulating element configured to contact a surface of a skin of the user and at least a portion of the bottom face of the electrically conductive layer to maintain the electrically conductive layer separated from the skin,
   wherein the area of the upper face of the electrically conductive layer and the electrically insulating element are pervious such that the manually-applied electrically conductive material that is applied to the area of the upper face of the electrically conductive layer is adapted to penetrate to the surface of the skin when the non-invasive electrode is worn by the user.

2. A wearable device comprising a non-invasive electrode for transcutaneous electrical stimulation or biological signal sensing of a user, the non-invasive electrode comprising:
   an electrically conductive layer operatively connectable to a device for at least one of delivering electrical current and sensing electrical signals, the electrically conductive layer configured to deliver an electrical current or sensing electrical signals, and having an upper face and a bottom face, the non-invasive electrode is adapted to be worn by the user such that an area of the upper face is exposed to an exterior environment for manual application of electrically conductive material;
   a garment comprising an electrically insulating element configured to contact a surface of a skin of the user and at least a portion of the bottom face of the electrically conductive layer to maintain the electrically conductive layer separated from the skin, wherein the area of the upper face of the electrically conductive layer and the electrically insulating element are pervious such that the manually-applied electrically conductive material that is applied to the area of the upper face of the electrically conductive layer is adapted to penetrate to the surface of the skin when the non-invasive electrode is worn by the user.

3. The electrode of claim 1, further comprising:
   a conductor operatively connected with the electrically conductive layer and operatively connectable with the device for at least one of delivering the electrical current and the sensing electrical signals.

4. The electrode of claim 3, wherein the conductor includes at least a part of the electrically conductive material.

5. The electrode of claim 1, wherein the electrically conductive material is a liquid or a gel.

6. The electrode of claim 5, wherein the electrically conductive material further includes:
an additive for optimizing at least one of an electrical conductivity of the electrically conductive material and a mechanical adhesion between the electrically conductive layer, the electrically insulating element, and the skin of the user.

7. The electrode of claim 5, wherein a physical state of a surface of the electrically conductive material that is not in contact with the skin forms a solid outer shell.

8. The electrode of claim 7, wherein the physical state of the surface of the electrically conductive material is modified via at least one of a heat exchange, a light drying, a photopolymerization, an oxidation, and evaporation of a liquid phase within the electrically conductive material, to form the solid outer shell.

9. The electrode of claim 7, wherein the electrically conductive material includes a radical initiator that, upon induction of at least one of a photo, thermo, and chemical activation, promotes a radical polymerization of the surface of the electrically conductive material that is not in contact with the skin.

10. The electrode of claim 5, wherein the electrically conductive material includes at least one of chemical compounds and medicinal products.

11. The electrode of claim 1, wherein the conductive layer and the insulating element are pervious such that at least a portion of the conductive layer and the insulating element include a network or mesh interspaced by empty spaces that permit a physical passage and electrical interconnection of the electrically conductive material.

12. The electrode of claim 11, wherein the electrically conductive material includes conductive particles that are smaller than the empty spaces of the network or mesh.

13. The electrode of claim 11, wherein the electrically conductive material includes insulating materials functionalized with electrically conductive elements.

14. The electrode of claim 1, wherein the area of the upper surface of the electrically conductive layer includes at least one of a color, symbol, number, word, or marker for distinction from other areas.

15. The electrode of claim 1, wherein the conductive layer and the electrically insulating element are pervious to allow penetration of the electrically conductive material from the upper face via the bottom face and via the electrically insulating element to the surface of the skin.

16. A system comprising several non-invasive electrodes, for transcutaneous electrical stimulation or biological signal sensing of a user, each of the non-invasive electrodes comprising:
an electrically conductive layer operatively connectable to a device for at least one of delivering electrical current and sensing electrical signals, the electrically conductive layer configured to deliver an electrical current or sensing electrical signals, and having an upper face and a bottom face, the non-invasive electrode is adapted to be worn by the user such that an area of the upper face is exposed to an exterior environment for manual application of electrically conductive material; and
an electrically insulating element configured to contact a surface of a skin of the user and at least a portion of the bottom face of the electrically conductive layer to maintain the electrically conductive layer separated from the skin,
wherein the area of the upper face of the electrically conductive layer and the electrically insulating element are pervious such that the manually-applied electrically conductive material that is applied to the area of the upper face of the electrically conductive layer is adapted to penetrate to the surface of the skin when the non-invasive electrode is worn by the user,
wherein the electrically insulating element of each non-invasive electrode is shared among the several non-invasive electrodes.

17. A wearable device comprising several non-invasive electrodes for transcutaneous electrical stimulation or biological signal sensing of a user, each of the non-invasive electrodes comprising:
an electrically conductive layer operatively connectable to a device for at least one of delivering electrical current and sensing electrical signals, the electrically conductive layer configured to deliver an electrical current or sensing electrical signals, and having an upper face and a bottom face, the non-invasive electrode is adapted to be worn by the user such that an area of the upper face is exposed to an exterior environment for manual application of electrically conductive material;
a garment comprising an electrically insulating element configured to contact a surface of a skin of the user and at least a portion of the bottom face of each of the electrically conductive layers of the several non-invasive electrodes to maintain each of the electrically conductive layers separated from the skin, wherein the area of the upper face of each of the electrically conductive layers and the electrically insulating element are pervious such that the manually-applied electrically conductive material that is applied to the area of the upper face of each of the electrically conductive layers is adapted to penetrate to the surface of the skin when the wearable device is worn by the user.

18. A system for transcutaneous electrical stimulation or biological signal sensing of a living being, the system comprising:
a non-invasive electrode configured to be placed on a skin of the living being; and
an electrically conductive viscous material for manual application to the non-invasive electrode,
wherein the non-invasive electrode includes,
an electrically conductive layer operatively connectable to a device for at least one of delivering electrical current and sensing electrical signals, the electrically conductive layer configured to deliver an electrical current or sensing electrical signals, and having an upper face and a bottom face, and the upper face having an area that is exposed to an exterior environment when the non-invasive electrode is worn by the living being for the manual application of the electrically conductive viscous material, and
an electrically insulating element configured to contact a surface of the skin of the living being and at least a portion of the bottom face of the electrically conductive layer to maintain the electrically conductive layer separated from the skin, the area of the upper face of the electrically conductive layer and the electrically insulating element are pervious such that the manually-applied electrically conductive viscous material that is applied to the area of the upper face of the electrically conductive layer is adapted to penetrate to the surface of the skin when the non-invasive electrode is worn by the living being.

19. The system of claim 18, wherein the area of the upper face of the electrically conductive layer includes at least one of a color, symbol, number, word, or marker for distinction from other areas.

20. A non-invasive electrode for transcutaneous electrical stimulation or biological signal sensing of a user, the electrode comprising:
- an electrically conductive layer operatively connectable to a device for at least one of delivering electrical current and sensing electrical signals, the electrically conductive layer configured to deliver an electrical current or sensing electrical signals, and having an upper face and a bottom face;
- an electrically insulating element configured to contact a surface of a skin of the user and at least a portion of the bottom face of the electrically conductive layer to maintain the electrically conductive layer separated from the skin; and
- an additional electrically insulating layer configured to at least partially cover the upper face of the electrically conductive layer, an upper face of the additional electrically insulating layer having an area that is exposed to an exterior environment when the non-invasive electrode is worn by the user for manual application of electrically conductive material, wherein the area of the additional electrically insulating layer, the electrically conductive layer, and the electrically insulating element are pervious such that the manually-applied electrically conductive material that is applied to the area of the upper face of the additional electrically insulating layer is adapted to penetrate to the surface of the skin when the non-invasive electrode is worn by the user.

21. The electrode of claim 20, wherein the area of the upper face of the additional electrically insulating layer includes at least one of a color, symbol, number, word, or marker for distinction from other areas.

* * * * *